United States Patent [19]
Kaufman et al.

[11] Patent Number: 4,860,885
[45] Date of Patent: Aug. 29, 1989

[54] LENS STORAGE SYSTEM

[75] Inventors: Herbert E. Kaufman, New Orleans, La.; Patricia M. Knight, Laguna Niguel; Shelley Buchen, Irvine, both of Calif.

[73] Assignee: Allergan, Inc., Irvine, Calif.

[21] Appl. No.: 187,840

[22] Filed: Apr. 29, 1988

[51] Int. Cl.⁴ ............................................. B65D 81/22
[52] U.S. Cl. ....................................................... 206/5.1
[58] Field of Search ........................................ 206/5.1

[56] References Cited

U.S. PATENT DOCUMENTS 3,298,502  12/1964  Schwartzman .
3,621,855  11/1971  Rabinowitz ........................... 206/5.1
4,623,249  11/1986  Grant .................................... 206/5.1
4,697,697  10/1987  Graham et al. ....................... 206/5.1

FOREIGN PATENT DOCUMENTS 631248  12/1961  Italy ....................................... 206/5.1

Primary Examiner—Joseph Man-Fu Moy
Attorney, Agent, or Firm—Gordon L. Peterson; Frank J. Uxa, Jr.

[57] ABSTRACT

A system useful for holding a lens device is disclosed and comprises: a chamber having a hollow interior space therein; a seal element capable of being placed in association with said chamber to substantially seal said interior space from the environment surrounding said chamber; a carrier assembly sized and adapted to carry a lens device and to be placed in said interior space; and an absorbent member located in said interior space and capable of carrying a material which is released into said interior space over a period of time.

37 Claims, 2 Drawing Sheets

U.S. Patent   Aug. 29, 1989   Sheet 1 of 2   4,860,885

LENS STORAGE SYSTEM

BACKGROUND OF THE INVENTION

This invention relates to a system for storing lens devices. More particularly, the invention relates to a system useful for storing or holding, e.g., for shipment, a lens device, e.g., a corneal tissue lens, a synthetic lens, a lens made of a blend of natural tissue and synthetic material and the like, prior to the lens device being associated with a living eye.

Corneal tissue lenses, such as epikeratophakia lenses, have been shipped either in a lyophilized (dry) state or in a liquid. Both of these shipping methods often result in damage to the lens, e.g., to the ultrastructure of the corneal stroma. It would be advantageous to have a new system for storing lens devices, such as corneal tissue lenses, which system would effectively allow shipment with reduced adverse effects on the lens device.

SUMMARY OF THE INVENTION

A new lens device storage and/or shipping system has been discovered. One basis of the present invention is the discovery that storing corneal tissue lenses in a chamber filled with vapor, preferably moist vapor, results in reduced swelling of the tissue, reduced damage to Bowman's membrane, reduced leaching of mucopolysaccharides and reduced collagen disruption. In view of these benefits, the present storage/shipping system is expected to provide outstanding clinical results, such as in faster visual recovery, faster epithelialization and fewer lens removals, relative to lenses shipped and/or stored using the previously described techniques.

In one embodiment, the invention involves a system useful for holding, e.g., for storage and/or shipment, a lens device, such as described above, in particular a corneal tissue lens. This system comprises a chamber, a seal means or element, a carrier means or assembly, and an absorbent means or member. The chamber has a hollow interior space. The seal element is capable of being placed in association with the chamber to substantially seal, or close, the interior space from the environment surrounding the chamber. The carrier assembly is sized and adapted to carry the lens device and to be placed in the interior space of the chamber. The absorbent member is also located in this interior space and is capable of carrying a material, preferably a liquid and more preferably an aqueous liquid, which is capable of being released into the interior space over a period of time.

The chamber may be constructed of any suitable, substantially non-interfering material, i.e., a material which is not substantially adversely affected by the other components of the system, does not substantially adversely affect such other components and which does not substantially adversely affect the lens device. A particularly useful material of construction for the chamber is borosilicate glass. The chamber preferably includes an opening through which the lens device can be placed into the interior space and removed from the interior space. The size, i.e., volume, of the interior space is not critical to the present invention. The size of the interior space should be sufficient to accommodate both the absorbent member and the carrier assembly (including the lens device). On the other hand, an excessively large interior space should be avoided to reduce the chance that the lens device may be damaged in the interior space. For example, if the interior space of the chamber is too large, the liquid from the absorbent member may be insufficient to maintain the proper or desired degree of hydration of the corneal tissue lens. It is preferred that such interior space have a volume in the range of about 1 cc. to about 100 cc., more preferably about 2 cc. to about 20 cc.

The seal element preferably acts in association with the opening of the chamber to substantially seal the interior space as described herein. Any suitable, substantially non-interfering material of construction may be used in the seal element. The seal element is movable relative to the chamber, e.g., removable from the chamber, to allow access to the interior space of the chamber. Preferably, the seal element is reusable. That is, the seal element is preferably structured so that it can be used to repeatedly seal and unseal the interior space. One useful material of construction for the seal element is silicone polymeric material.

The carrier assembly is preferably removable from the interior space. Any substantially non-interfering material of construction may be used in the carrier assembly. For example, the carrier assembly may be made of polycarbonate. The carrier assembly should be structured so that the lens device is exposed to the vapor within the interior space of the chamber. Preferably, the carrier means is structured and sized so that the lens device does not come into direct contact with the liquid in the absorbent member. In one particularly useful embodiment, the carrier assembly includes a first component and a second component sized and adapted so that the lens device can be located therebetween. However, even with the lens located between these two carrier assembly components, the lens should be exposed to the vapor within the interior space of the chamber. An equilibrium is preferably established between the lens device and this vapor, more preferably a moist (i.e., water-containing) vapor, so that the lens device is suitably maintained, e.g., at the desired degree of hydration, in the substantially sealed interior space.

In a particularly useful embodiment, the first and second components of the carrier assembly each have a centrally located through hole. Further, these components are configured so that when they are coupled together, at least one other hole (other than the centrally located through holes), and preferably a plurality of such other holes, is (are) apparent through the coupled structured in fluid communication with the location of the lens device between the coupled components. These through holes and other hole or holes are very effective in exposing the lens device to the vapor inside the interior space.

The first and second components can advantageously be structured substantially identically. This simplifies and makes easier the manufacture of the carrier assembly, since the same part can be used for each of the carrier components.

An especially useful carrier assembly structure involves a first component with a first end and a projection extending outwardly a first distance from the first end; and a second component with a second end. A recess extends inwardly a second distance from the second end, and includes at least one, preferably a plurality of, laterally extending openings. The second distance is greater than the first distance, and the projection of the first component is insertable into the recess of the second component to couple the first and second components together. This structure allows effective exposure of the lens device to the vapor in the chamber. It is especially useful if the first and second components are structured substantially identically. That is, it is advantageous if both the first and second components have both first and second ends, projections and recesses, as described above.

As noted above, the absorbent member is located in the interior space and is capable of carrying a material, preferably a liquid and more preferably an aqueous liquid, which is capable of being released into the interior space over a period of time, e.g., to aid in effectively maintaining the lens device during storage and/or shipment. For example, where, as is preferred, the absorbent material is wetted with liquid, in particular an aqueous liquid, the liquid from the absorbent member vaporizes into the vapor space of the interior space and contacts the lens device, preferably to substantially maintain the degree of hydration of the lens during storage and/or shipment.

The absorbent member is preferably substantially saturated with a liquid, more preferably an aqueous liquid. By "saturate" as used herein is meant that the absorbent member can carry no additional liquid within its structure without liquid becoming physically disassociated or separated from the absorbent member. In one particularly useful embodiment, the liquid carried by the absorbent member is an antibiotic aqueous liquid, e.g., an antibiotic aqueous solution, including one or more antibiotic agents. The release of such antibiotic liquids from the absorbent member into the sealed interior space acts to reduce bacterial damage to the lens device which might be caused by the environment present in the sealed interior space. Particularly useful antibiotic agents include a triple antibiotic of neomycin sulfate, polymyxin B sulfate and gramicidin; gentamicin; and the like.

Any suitable, substantially non-interfering material may be used to form the present absorbent member. Preferably, the material chosen has at least some capacity to absorb liquid and to release it into the sealed interior space over a period of time. Examples of suitable materials from which the absorbent member can be made include natural and synthetic sponges, polymeric foams, fabrics, fibers, and mixtures thereof. One particularly useful material of construction for the absorbent member is a mass of cotton fibers, for example, configured into a pad.

A method for storing a lens device, in particular a corneal tissue lens, in a chamber may be practiced using the present system. Such method, in one broad aspect, comprises placing an absorbent member, wet with liquid, in the interior space of a chamber; placing and maintaining the lens device in the interior space away from the absorbent member and exposed to the vapor in the interior space; and substantially sealing the interior space from the environment surrounding the chamber. The lens device is preferably exposed to the vapor inside the interior space so that a substantial equilibrium is reached between the vapor and the lens device so that the device suffers no substantial damage during storage, i.e., so that the lens device (corneal tissue lens) is still usable for its intended purpose after storage.

Preferably, the liquid from the absorbent member is vaporized in the interior space over a period of time. The liquid is preferably aqueous based and more preferably includes one or more antibiotic agents, e.g., as described above. At the time the lens device, preferably a corneal tissue lens, is placed in the interior space, it is preferably at least partially hydrated, more preferably substantially totally hydrated. The term "hydrated" as used herein refers to a condition in which water is included in the structure of the lens device, e.g., corneal tissue lens.

These and other aspects and advantages of the present invention are set forth in the following detailed description and claims, particularly when considered in conjunction with the accompanying drawings in which like parts bear like reference numerals.

DETAILED DESCRIPTION OF THE DRAWINGS

Figure 1:
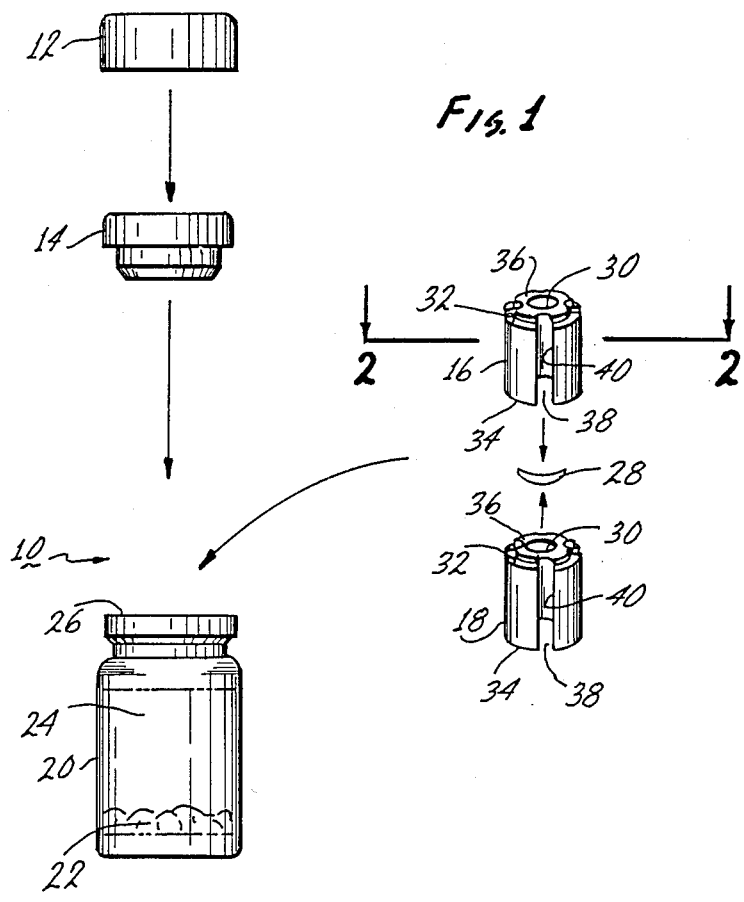
FIG. 1 is in front, exploded view showing one embodiment of the present system for use with a corneal tissue lens.
Figure 2:
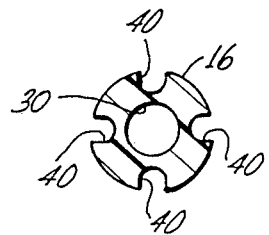
FIG. 2 is a cross-sectional view taken along line 2—2 of FIG. 1.
Figure 3:
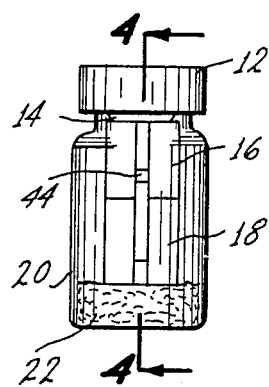
FIG. 3 is a front view of the embodiment shown in FIG. 1. as is appears fully assembled.

Referring now to the drawings, a lens package, shown generally as 10, for a corneal tissue lens includes a crimp cap 12, a stopper 14, a first carrier component 16, a second carrier component 18, a vial 20 and a mass or pad of cotton fibers 22.

Vial 20 is made of borosilicate glass and includes a hollow interior space 24 and a top opening 26. Interior space 24 is about 10 cc in volume when stopper 14 is in place in top opening 26.

Stopper 14 is made of silicone polymer and is sized to fit into top opening 26 to completely seal interior space 24 from the atmosphere or environment outside vial 20. Stopper 14 is structured to be an effective seal, yet it is relatively easy to remove from top opening 26, as desired, to gain access to interior space 24. In addition, stopper 14 can be used repeatedly to reseal interior space 24, as desired. Thus, if desired, the package 10 can be repeatedly reused, although care should be exercised to avoid contamination each time package 10 is used with a different corneal tissue lens.

Crimp cap 12 is placed over stopper 14 and adjacent top opening 26. Crimp cap 12 acts to protect stopper 14, to substantially prevent leakage of vapor from interior space 24 and to reduce the risk of accidentally dislodging stopper 14 from top opening 26.

First carrier component 16 and second carrier component 18 are each made of polycarbonate, and together are structured to hold corneal tissue lens 28 between them. First and second carrier components 16 and 18, respectively, are adapted to hold lens 28 loosely in place and are structured to allow lens 28 to be exposed to the atmosphere within interior space 24. This feature preferably allows lens 28 to be in substantial equilibrium with the environment inside interior space 24.

Figure 4:
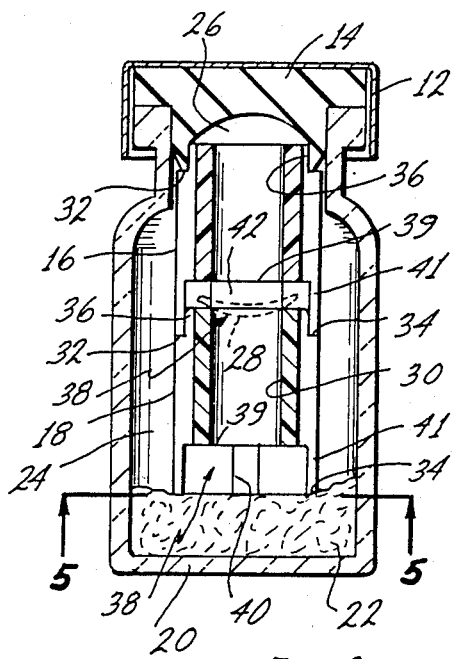
FIG. 4 is a cross-sectional view taken along line 4—4 of FIG. 3.
Figure 5:
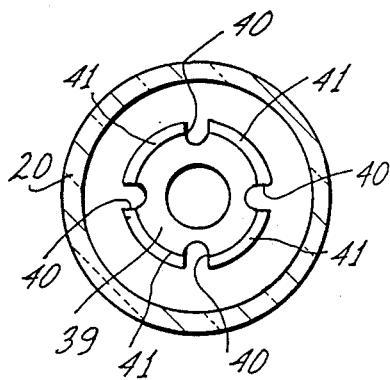
FIG. 5 is a cross-sectional view taken along line 5—5 of FIG. 4.

First carrier component 16 and second carrier component 18 are structured identically. Each of these components includes a central through hole 30, a first end 32 and a second end 34. Further, each of these components include a projection 36 which extends outwardly from first end 32, and a recess 38 which extends inwardly from second end 34 and terminates at an annular wall 39. The recess 38 extends inwardly from the second end 34 a greater distance than the distance projection 36 extends from first end 34. A series of four (4) laterally extending notches 40 are placed equidistantly around the periphery of each of first and second carrier components 16 and 18, and extend from the first end 32 to the second end 34 of such carrier component. These notches 40 form legs 41, which together with wall 39 define recess 38. Projection 36 of one of the carrier components is sized to be insertable into recess 38 of the other of the carrier components with a friction fit to provide a releasably coupled assembly which is sufficiently long so that it can not lay on its side in interior space 24. This feature keeps corneal tissue lens 28 out of direct contact with cotton pad 22. Preferably, stopper 14 contacts the coupled assembly, as shown in FIG. 4, to stabilize the position of the coupled assembly in interior space 24.

Corneal tissue lens 28 is introduced into package 10 in an at least partially, preferably substantially fully, hydrated state. This state is distinct from the lyophilized state in which such lenses have been packaged in the past. Also, lens 28 is exposed to the vapor in interior space 24. Thus, the package 10 is distinct from other prior systems in which corneal tissue lenses were packaged in liquid.

Cotton pad 22 is located at the bottom of interior space 22 and is substantially completely saturated with an aqueous solution containing an antibiotic agent known to be effective in maintaining corneal tissue lens 28 free from harmful microbial infestations.

Package 10 functions as follows. Initially all the components of package 10 are sterilized or otherwise sanitized to reduce the risk of harming corneal tissue lens 28. Cotton pad 22 is placed at the bottom of interior space 24 through top opening 26. First and second carrier components 16 and 18 are assembled, as described above, with corneal tissue lens 28 situated therebetween in compartment 42 formed by inserting projection 36 of second carrier component 18 into recess 38 of first carrier component 16. Compartment 42 is sized to hold corneal tissue lens 28 loosely, without damaging the lens. Thus, the lens 28 may move to some extent in compartment 42. However, lens 28 cannot flip over or escape from compartment 42 while first carrier component 16 and second component 18 remain assembled.

When assembled the carrier includes through holes 30 and a series of four (4) side holes 44 equidistantly spaced around the periphery of the assembled carrier. The notches 40 of first carrier component 16 can be aligned with the notches 40 of second carrier component 18. through holes 30 and side holes 44 exposes as least a portion of corneal tissue lens 28 to the vapor inside interior space 24. This assembled carrier is also placed into interior space 24 through top opening 26. A quantity of aqueous antibiotic solution is applied to cotton pad 22 to substantially completely saturate cotton pad 22 with this solution. Except for this liquid associated with cotton pad 22, the atmosphere within interior space 24 is gaseous. Stopper 14 is placed in top opening 26 to seal interior space 24 and crimp cap 12 is placed over stopper 14.

The thus completely assembled package 10 is effective to store and/or ship corneal tissue lens 28. To gain access to corneal tissue lens 28, crimp cap 12 and stopper 14 are removed from top opening 26. The lens carrier assembly is then removed from interior space 24 through top opening 26. First and second carrier components 16 and 18 are disassembled at which point corneal tissue lens 28 is accessible and ready for use.

Maintaining corneal tissue lens 28 in moist interior space 24 results in reduced tissue swelling, reduced damage to Bowman's membrane, reduced leaking of mucopolysaccharides and reduced collagen disruption. With reduced damage to corneal tissue lens 28, improved surgical or clinical results are expected using corneal tissue lens 28 stored using the present system and method.

EXAMPLES

A series of tests were conducted to compare the present system of storing lens devices to storing in a liquid medium and storing in the lyophilized (dry) state.

Human eye bank corneas rejected from manufacturing due to anterior surface defects were used for all tests. All tissues were processed identically up to the point of storage. This processing involved first removing the epithelium and endothelium by gentle scraping using a microsponge. Tissues were then stained in a green dye solution to aid visualization at the cryolathe. Tissues were pressed to normal dimensions and hydration using a corneal press. After pressing, the corneas were cryolathed to a plano thickness of 0.2–0.3 mm. After cryolathing, the tissues were thawed briefly in a balanced salt solution (BSS).

After thawing in BSS, a number of the corneal specimens were stored in a system similar to that shown in FIG. 4. In this package the two carrier components when assembled provide a 2 mm compartment to hold the tissue. The assembled carrier was then placed into a borosilicate vial containing a cotton ball saturated with a triple antibiotic of neomycin sulfate, polymyxin B sulfate and gramicidin in water. The vial was stoppered with a medical-grade silicone stopper and sealed with a crimp cap. All tissues were stored refrigerated at 4±3° C. Corneal specimens to be stored in liquid media were placed directly into such media after thawing. Each of these liquid media, referred hereafter as Liquid 1 and Liquid 2, is used commercially to store corneal tissue. A series of the corneal specimens were stored in the lyophilized (dry) state.

To monitor tissue thickness during storage, an electronic tissue thickness gauge such as has been used with hydrogel contact lenses was utilized. The thickness of each specimen was initially measured immediately after thawing in BSS.

After 3, 7 or 14 days, the thickness of each tissue was again measured. For tissues stored in Liquid 1 and Liquid 2, each of four tissues was measured at each timepoint after excess surface moisture was removed with a microsponge. For tissues stored in the present system, 15 tissues were studied, five at each timepoint.

Results of the tissue thickness measurements are shown in Table 1. Although there was no significant difference in the initial tissue thicknesses of all samples, tissues stored in Liquid 1 and Liquid 2 swelled significantly more than tissues stored in the present system over the 14-day storage period. While thickness values remained unchanged in the present system, Liquid 1 tissues had an average tissue thickness increase of 107% to 111%, and Liquid 2 tissues had an average tissue thickness increase ranging from 93% to 100%.

Light microscopy analysis using toluidine blue/basic fuchsin staining indicated that tissues stored in the present system had the highest stain uptake, with Liquid 2 tissues having the lowest stain uptake. Tissues stored in Liquid 1, and particularly those stored in Liquid 2, structure better than lyophilization, Liquid 1 storage, or Liquid 2 storage.

TABLE 1

Tissue Thickness Using Various Storage Methods

| Storage System | Storage Time (days) | Number of Tissues | Initial Thickness (mm ± SD) | Final Thickness (mm ± SD) | Percent Change |
|---|---|---|---|---|---|
| PRESENT INVENTION | 3.0 | 4 | 0.29 ± 0.02 | 0.29 ± 0.02 | +0.0 |
|  | 7.0 | 5 | 0.28 ± 0.02 | 0.28 ± 0.04 | +0.0 |
|  | 14.0 | 5 | 0.29 ± 0.02 | 0.29 ± 0.06 | +0.0 |
| LIQUID 1 | 2.8 | 4 | 0.27 ± 0.06 | 0.57 ± 0.10 | +111.1 |
|  | 6.8 | 4 | 0.27 ± 0.06 | 0.56 ± 0.12 | +107.4 |
|  | 14.1 | 4 | 0.27 ± 0.06 | 0.56 ± 0.12 | +107.4 |
| LIQUID 2 | 2.9 | 4 | 0.27 ± 0.04 | 0.53 ± 0.10 | +96.3 |
|  | 6.9 | 4 | 0.27 ± 0.04 | 0.52 ± 0.10 | +92.6 |
|  | 12.8 | 4 | 0.27 ± 0.04 | 0.54 ± 0.10 | +100.0 |

While this invention has been described with respect to various specific examples and embodiments, it is to be understood that the invention is not limited thereto and that it can be variously practiced within the scope of the following claims.

appeared edematous and extracted. Ligh microscopy sections further supported the tissue thickness measurements described previously. That is, the tissues stored in the present system were consistently thinner and less edematous when compared to Liquid 1 and Liquid 2 tissues. Rehydrated lyophilized tissues were also thinner and less edematous that Liquid 1 and Liquid 2 tissues. Rehydrated lyophilized tissues were similar in thickness to tissues stored in the present system.

Tissues stored in the present system were observed to retain a stromal collagen ultrastructure with little or no ground substance condensation or extraction. Little to no edema and no vacuolization was observed. Storage time did not appear to be a factor over the two-week study period. Bowman's membrane was also well-preserved, with little to no ground substance condensation or extraction.

Lyophilized tissues showed some loss of ultrastructure with ground substance condensation and extraction of the stroma and Bowman's membrane evident in all samples. Vacuolation of the stroma was evident in many of the samples. Storage time did not appear to be a factor.

Liquid 1 tissues showed good retention of stromal collagen ultrastructure, although stromal edema was evident. In addition, progressive ground substance in Bowman's membrane was noted. The Liquid 1 tissue was noticeably extracted by 14 days when compared to the tissue stored in the present system.

Liquid 2 tissues showed good collagen structure, but stromal edema was noted. Bowman's membrane also showed progressive extraction of the ground substance. Comparison to the other tissues studied demonstrated Liquid 2 tissues to have the most extraction of ground substance in Bowman's membrane.

Analysis of all four storage methods demonstrated the present storage/shipping system to have the best overall retention of ground substance matrix and collagen ultrastructure. Liquid 1 tissues were ranked second, followed by Liquid 2 tissues and lyophilized tissues.

In summary, swelling studies demonstrated a statistically significant difference between tissues stored in a present system versus tissues stored in Liquid 1 and Liquid 2. Tissue swelling could cause a loss of mucopolysaccharides from the epikeratophakia lens as well as disrupt the collagen ultrastructure. Storage in the present system appears to preserve the tissue ultra-

What is claimed is:

1. A system useful for holding a lens device comprising:
   a chamber having a hollow interior space therein;
   seal means capable of being placed in association with said chamber to substantially seal said interior space from the environment surrounding said chamber;
   absorbent means located in said interior space and capable of carrying a material which is capable of being released into said interior space over a period of time and;
   carrier means sized and adapted to carry a lens device and to be placed in said interior space so that the lens device being carried by said carrier means is out of direct contact with said absorbent means and is exposed to the material released into said interior space.

2. The system of claim 1 wherein said chamber includes an opening through which said lens device is removed from said interior space.

3. The system of claim 2 wherein said seal means acts in association with said opening to substantially seal said interior space from the environment surrounding said chamber.

4. The system of claim 1 wherein said carrier means is removable from said interior space.

5. The system of claim 1 wherein said carrier means includes a first component and a second component sized and adapted so that said lens device can be located therebetween.

6. The system of claim 1 wherein said absorbent means is wet with liquid.

7. The system of claim 1 wherein said absorbent means is substantially saturated with liquid.

8. The system of claim 6 wherein said liquid is an antibiotic liquid.

9. The system of claim 6 wherein said liquid is an aqueous antibiotic liquid.

10. The system of claim 1 wherein said absorbent means is made from a substance selected from the group consisting of natural and synthetic sponges, polymeric foams, fabrics, fibers and mixtures thereof.

11. The system of claim 1 wherein said carrier means is configured and placed within said interior space so that said lens device is in contact with the vapor in said interior space.

12. A system comprising:

a lens device to be stored prior to being associated with a living eye a chamber having a hollow interior space therein and an opening through which said lens device is removed from said interior space;

seal means associated with said opening to substantially seal said interior space from the environment surrounding said chamber;

absorbent means located in said interior space and carrying a material which is capable of being released into said interior space over a period of time and;

carrier means located in said interior space, and sized and adapted to carry said lens device out of direct contact with said absorbent means and to expose said lens device to the vapor in said interior space.

13. The system of claim 12 wherein said lens device is a corneal tissue lens.

14. The system of claim 13 wherein said corneal tissue lens is at least partially hydrated.

15. The system of claim 13 wherein said corneal tissue lens is substantially fully hydrated.

16. The system of claim 12 wherein said carrier means is removable from said interior space.

17. The system of claim 12 wherein said carrier means includes a first component and a second component sized and adapted so that said lens device can be located therebetween and exposed to the vapor in said interior space.

18. The system of claim 12 wherein said absorbent means is wet with liquid.

19. The system of claim 12 wherein said absorbent means is substantially saturated with liquid.

20. The system of claim 18 wherein said liquid is an antibiotic liquid.

21. The system of claim 18 wherein said liquid is an aqueous antibiotic liquid.

22. The system of claim 12 wherein said absorbent means is made from a substance selected from the group consisting of natural and synthetic sponges, polymeric foams, fabrics, fibers and mixtures thereof.

23. A method for storing a lens device in a chamber comprising:

placing an absorbent member in the interior space of said chamber, said absorbent member in said chamber being wet with a liquid;

placing and maintaining said lens device in said interior space of said chamber out of direct contact with said absorbent member and exposed to the vapor in said interior space; and substantially sealing said interior space from the environment surrounding said chamber.

24. The method of claim 23 wherein said liquid is vaporized in said interior space over a period of time.

25. The method of claim 23 wherein said lens device in said interior space is at least partially hydrated.

26. The method of claim 23 wherein said lens device is substantially fully hydrated.

27. The method of claim 23 wherein said lens device is a corneal tissue lens.

28. The method of claim 23 wherein said absorbent member in the interior space of said chamber is substantially saturated with said liquid before said internal space is substantially sealed.

29. The method of claim 23 wherein said liquid is an antibiotic liquid.

30. The method of claim 28 wherein said liquid is an aqueous antibiotic liquid.

31. An assembly for carrying a lens device comprising: a first component and a second component sized and adapted to be coupled together so that a lens device can be located therebetween, each of said first and second components having a centrally located through hole and being configured so that when said first and second components are coupled at least one other hole is apparent through the coupled structure in fluid communication with the location of said lens device between said coupled first and second components.

32. The assembly of claim 31 wherein a plurality of said other holes are apparent.

33. The assembly of claim 31 wherein said first and second components are structured substantially identically.

34. The assembly of claim 31 wherein said first component has a first end and a projection extending outwardly a first distance from said first end, and said second component has a second end and a recess extending inwardly a second distance from said second end and including at least one laterally extending opening, said second distance being greater than said first distance, and said projection of said first component being insertable into said recess of said second component to couple said first and second components.

35. The assembly of claim 34 wherein said recess includes a plurality of said laterally extending openings.

36. The assembly of claim 34 wherein said first and second components are structured substantially identically.

37. The assembly of claim 35 wherein said first and second components are structured substantially identically.

* * * * *